United States Patent [19]

Gilpin

[11] 4,433,155

[45] Feb. 21, 1984

[54] INHIBITORS FOR FURFURALS

[75] Inventor: Jo Ann Gilpin, Midland, Mich.

[73] Assignee: The Dow Chemical Company, Midland, Mich.

[21] Appl. No.: 382,874

[22] Filed: May 28, 1982

[51] Int. Cl.$^3$ .................. C07D 307/46; C07D 307/48
[52] U.S. Cl. .................................... 549/205; 549/483; 549/489; 549/490
[58] Field of Search ................ 549/205, 483, 489, 490

[56] References Cited

U.S. PATENT DOCUMENTS

| | | | |
|---|---|---|---|
| 2,922,777 | 1/1960 | Burgert | 524/114 X |
| 2,959,566 | 11/1960 | Burgert | 524/114 |
| 2,993,903 | 7/1961 | Kraus | 549/205 X |
| 3,953,478 | 4/1976 | Baker | 549/205 |
| 4,154,744 | 5/1979 | Hamada | 549/489 |

OTHER PUBLICATIONS

H. H. Szmant et al., J. Chem. Tech. Biotechnol. 31, 205-212, (1981).
A. P. Dunlop et al., Ind. Eng. Chem. 38, 705-708 (1946).
A. P. Dunlop et al., The Furans, ACS Monograph Series, Reinhold (1953), pp. 384-387.

*Primary Examiner*—Richard Raymond
*Attorney, Agent, or Firm*—Douglas N. Deline

[57] ABSTRACT

Furfural or derivatives thereof, especially 5-chloromethyl furfural, is inhibited against the formation of resinous decomposition products by addition of epoxy compounds such as the reaction product of epichlorohydrin and bisphenol A.

11 Claims, No Drawings

INHIBITORS FOR FURFURALS

BACKGROUND OF THE INVENTION

The present invention relates to a process for preventing destructive oligomer or polymer formation in furfural and substituted furfural solutions. More particularly, the present invention is concerned with preventing such resinification of highly unstable 5-chloromethyl furfural by addition of an epoxy resin thereto.

A. P. Dunlop et al., *Ind. Eng. Chem.*, 38, 705 (1946), disclosed that discoloration of furfural solutions due to auto-oxidation is avoided by the use of tertiary amines and phenolic antioxidants such as hydroquinone.

In U.S. Pat. No. 4,154,744, a process for the preparation of furan derivatives such as furfural, methyl furfural and chloromethyl furfural is disclosed. The compounds are obtained by acid decompositions of saccharides such as glucose, fructose, and saccharose, and are useful as intermediates for medicines and agricultural chemicals. The disclosed process employs a surfactant as an aid in preventing resinification of the furfural derivatives by the formation of a micelle-like state in the reaction mixture. The above U.S. Pat. No. 4,154,744 is herein incorporated by reference in its entirety.

It is known to add epoxy-containing compounds to polyvinyl chloride-containing resins to inhibit degradation of such polymers at elevated temperatures. The epoxies stabilize the polymer by reacting with HCl as it is released from the polyvinyl chloride resin preventing it from catalyzing further decomposition.

Despite the use of care in the preparation of the above furfural derivatives, the use of prior known methods of preventing the formation of unacceptable amounts of oligomer products in furfural derivatives made by the above process have proven unacceptable. In particular, where it is desired to provide highly pure compounds it is often advantageous to distill or otherwise purify the furfural product prior to use. Such procedures disadvantageously remove inhibitors such as soaps or surfactants or severely reduce the amounts present. At the same time, such procedures, especially distillation, expose the furfural derivatives to elevated temperatures that enhance the rate of resin formation. In addition, it has been found that the acidic conditions of reaction employed in preparation of the furfural compounds introduce small amounts of acid contamination into the desired product. This acid contamination, particularly hydrogen chloride contamination, is believed to contribute to the above-described resin formation problem through acid induced resinification.

It would be desirable to provide a process for preventing or reducing the formation of resinous reaction products of furfural compounds.

It would further be desirable to inhibit the formation of resinous reaction products of furfural compounds formed by acid induced resinification.

Additionally, it would be desirable to provide a process to inhibit the resinification of highly unstable 5-chloromethyl furfural.

SUMMARY OF THE INVENTION

These and other objects of the invention that will become apparent to the skilled artisan are accomplished according to the present invented process. Accordingly, a process for the prevention or reduction of resinification of furfural or derivatives thereof is provided comprising combining with the furfural or derivative thereof an effective amount to prevent resin formation of an epoxy compound.

DETAILED DESCRIPTION OF THE INVENTION

The furfural compounds preferably inhibited to resin formation according to the present invention are those formed by acid, particularly hydrochloric acid, decomposition of saccharides such as xylose, ribose, arabinose, rhamnose, fucose, glucose, galactose, mannose, fructose, sorbose, saccharose, maltose, lactose, etc. A most preferred furfural compound is 5-chloromethyl furfural.

The epoxy compounds added to the above furfurals to prevent resinification include aliphatic and aromatic compounds containing vicinal epoxide functionality and optionally further containing ether or carbonyl functionality. Preferably, the epoxy compounds are resins of low volatility that are not readily lost from the furfural solution by vaporization, e.g., resins having a vapor pressure less than that of the furfural compounds to which they are added. Suitable epoxy compounds include: epoxy derivatives of fatty acids; aliphatic glycidyl ethers such as tertiary butyl glycidyl ether, isopropyl glycidyl ether, tertiary amyl glycidyl ether and mono- or polyglycidyl ether derivatives of polyols or polyol ethers such as glycerine, (poly)alkylene glycols and monoethers of poly(alkylene) glycols; aromatic glycidyl and polyglycidyl ethers such as reaction products of phenols or bisphenols with epichlorohydrin, e.g., glycidyl or diglycidyl ether derivatives of phenolic compounds such as phenol, hydroquinone, 4,4'-dihydroxybiphenyl, 3,3',5,5'-tetraalkyl-4,4'-dihydroxybiphenyl, bisphenol A, novolac, etc.; and carbonyl-containing epoxy derivatives of the formula:

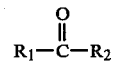

wherein $R_1$ is an epoxy-substituted aliphatic or aromatic moiety of up to about 20 carbons; and $R_2$ is hydrogen or a radical of up to about 20 carbons selected from the group consisting of aliphatic, aromatic and $R_1$.

The latter class of carbonyl-containing compounds include: 4-(2,3-epoxypropoxy)-2-hydroxybenzophenone, 4'-(2,3-epoxypropoxy)-2-hydroxybenzophenone, 4,4'-bis(2,3-epoxypropoxy)-2-hydroxybenzophenone, etc. Also included are further polymeric or copolymeric reaction products such as partially polymerized products of the above epoxy compounds, e.g., epoxy resins.

Preferred epoxy-containing compounds are liquid epoxy resins that are diglycidyl ethers of aromatic dihydroxyl compounds, especially diglycidyl ethers of bisphenol A.

The epoxy compounds are added to the furfural compound in minor amounts, generally from about 0.01 percent to about 10.0 percent by weight, preferably 0.1 percent to 2.0 percent by weight based on the furfural compound. They may be added both before or after distillation and may be combined with other solvents or employed in combination with other processing techniques. For example, it is convenient to employ toluene or other aromatic solvents to dissolve the furfural compounds. Epoxy resins may also be combined with such solutions in order to inhibit the resinification of the furfural compound while in solution.

It is possible to treat the furfural compounds with decolorizing or purifying agents in addition to inhibiting resinification and discoloration by use of epoxy compounds. For example, the furfural compound or a solution thereof may be treated with such agents as charcoal, clays or carbon black either before or after addition of the epoxy compound and the purified product recovered by distillation, filtration or other separation means. Additional inhibitors and antioxidants such as soaps, surfactants, amines or phenolic antioxidants may also be employed in combination with the epoxy compounds of the invention. It is also known that elevated temperatures increase the rate of formation of resin. Furfural compounds, especially chloromethyl furfural, inhibited according to the present invention are preferably retained at reduced temperatures less than about 30° C.

SPECIFIC EMBODIMENTS

Having described the invention, the following examples are provided as further illustrative and are not to be construed as limiting.

EXAMPLE 1

5-Chloromethyl furfural was prepared by reaction of fructose with concentrated hydrochloric acid in toluene in a well-stirred two-phase system. The reaction was conducted at 85° C. for 10 minutes. The product was recovered by decanting the organic layer and removing toluene under vacuum.

EXAMPLE 2

Samples of the 5-chloromethyl furfural of Example 1 were treated as further indicated in Table I and stored in stoppered glass vials at uniform temperatures. After the indicated time period, the samples were examined for evidence of resin formation by redissolving the sample in toluene, separating the insoluble resin by filtration and weighing the amount of recovered resin. Run 4 represents a sample treated according to the instant invention.

TABLE I

| Run | Treatment | Storage Temp (°C.) | Time (months) | Amount of Resin Formation % |
|---|---|---|---|---|
| 1 | none | 25 | 5 | 100 |
| 2 | charcoal[1] | 25 | 9 | 1 |
| 3 | charcoal[1] | −10 | 9 | 0 |
| 4 | charcoal/epoxy[2] | 25 | 9 | 0 |
| 5 | charcoal/distillation[3] | 25 | 9 | 100 |
| 6 | CaCO$_3$[4] | 25 | 5 | 100 |
| 7 | Ca Stearate[4] | 25 | 5 | 100 |
| 8 | myrcene[4] | 25 | 5 | 100 |
| 9 | Ionol[4] | 25 | 5 | 100 |
| 10 | butylene oxide[4] | 25 | 5 | 100 |

TABLE I-continued

[1]Bone charcoal (~10 weight percent) added to toluene solution, stirred for approximately 30 minutes, removed by filtration and toluene removed by vacuum.
[2]Same as 1 but 0.6 weight percent DER ® 383, an epoxy resin formed by the reaction of epichlorohydrin and bisphenol A available from The Dow Chemical Company, was added to product.
[3]Same as 1 but product was purified by distillation at 68° C.-69° C. @ 0.7 torr.
[4]Comparative tests - inhibitor added to product after removal of toluene solvent.

It is seen that the sample of Run 4 contained less resin (0 percent vs 1 percent) than a similarly treated sample that was not inhibited by addition of an epoxy resin. The inhibited sample retained at room temperature possessed the same purity as an uninhibited sample retained at −10° C. The best inhibition is obtained by both charcoal treatment and addition of epoxy resin inhibitor. Reexamination of all samples after about 20 months indicated that complete resinification of all samples does eventually occur regardless of the presence of the inhibitor.

EXAMPLE 3

Further samples of 5-chloromethyl furfural prepared according to Example 1 were purified by vacuum stripping of toluene and distillation at 68° C.-69° C. (0.7 torr). One sample was stabilized prior to distillation by addition of 0.3 weight percent DER ® 383. Upon distillation the unstabilized sample formed substantial quantities of char and gave reduced levels of purified product compared to the stabilized sample. The stabilized sample distilled smoothly to a nearly dry pot with no evidence of char formation.

What is claimed is:

1. A process for inhibiting or reducing resinification of furfural or derivatives thereof comprising combining with the furfural or derivative thereof an effective amount to prevent or reduce resin formation of an epoxy compound.

2. The process of claim 1 wherein the furfural derivative is 5-chloromethyl furfural.

3. The process of claim 1 wherein the amount of epoxy compound combined is from about 0.01 percent to about 10 percent by weight.

4. The process of claim 1 wherein the epoxy compound is an epoxy resin having a vapor pressure less than that of the furfural compound with which it is combined.

5. The process of claim 1 wherein the epoxy compound is a glycidyl or diglycidyl ether derivative of a phenolic compound.

6. The process of claim 5 wherein the epoxy compound is the reaction product of epichlorohydrin and bisphenol A.

7. The process of claim 1 wherein in addition the furfural or derivative is treated with a decolorizing or purifying agent.

8. A composition comprising furfural or a derivative thereof and an effective amount to prevent resin formation of an epoxy compound.

9. A composition according to claim 8 wherein the epoxy compound is present in an amount from about 0.01 percent to about 10 percent by weight.

10. A composition according to claim 8 wherein the furfural derivative is 5-chloromethyl furfural.

11. A composition according to claim 10 wherein the epoxy compound is the reaction product of epichlorohydrin and bisphenol A.

* * * * *